(12) United States Patent
Chen

(10) Patent No.: US 6,377,170 B1
(45) Date of Patent: Apr. 23, 2002

(54) SIGNAL EMITTER HAVING A TESTING DEVICE

(76) Inventor: Ming Der Chen, 10F-6, No. 666, Sec. 2, Wu Chuan West Road, Taichung (TW)

(*) Notice: Subject to any disclaimer, the term of this patent is extended or adjusted under 35 U.S.C. 154(b) by 0 days.

(21) Appl. No.: 09/678,240

(22) Filed: Oct. 4, 2000

(51) Int. Cl.⁷ .............................................. G08B 29/00
(52) U.S. Cl. ................ 340/514; 340/572.8; 340/693.8; 340/825.19
(58) Field of Search ................. 340/514, 507, 340/572.1, 572.8, 693.7, 693.8, 825.19

(56) References Cited

U.S. PATENT DOCUMENTS

| | | | |
|---|---|---|---|
| 4,406,290 A | * | 9/1983 | Walbeoffe-Wilson et al. .... 128/689 |
| 5,771,001 A | * | 6/1998 | Cobb ...................... 340/573.1 |
| 6,067,006 A | * | 5/2000 | O'Brien ................... 340/384.1 |
| 6,278,441 B1 | * | 8/2001 | Gouzman et al. ........... 345/163 |

* cited by examiner

*Primary Examiner*—Daryl Pope
(74) *Attorney, Agent, or Firm*—Charles E. Baxley

(57) ABSTRACT

An emitter includes a housing for attaching to a user and for receiving a control circuit having one or more CPUs, a memory coupled to the CPU, a sensing circuit coupled to the CPU for sensing a voltage supplied to the CPU, an emitting circuit coupled to the CPU for being actuated by the CPU to emit a signal out. The housing includes two switches coupled to the CPU, and two further switches for information entering purposes. The emitting circuit may send out the signal by actuating the switches. The functions of the emitter may be tested with the switches.

1 Claim, 3 Drawing Sheets

SIGNAL EMITTER HAVING A TESTING DEVICE

BACKGROUND OF THE INVENTION

1. Field of the Invention

The present invention relates to an emitter, and more particularly to an emitter for emitting a warning or an emergency signal.

2. Description of the Prior Art

More and more old people live along nowadays, without being cared. People may not easily and quickly find the old people when they need help or after they are dead. U.S. Pat. No. 5,771,001 to Cobb discloses one of the typical personal alarm system. However, the typical alarm system may not be tested whether the functions of the alarm system work or not.

The present invention has arisen to provide an emitter for allowing people to emit a warning signal or an emergency signal.

SUMMARY OF THE INVENTION

The primary objective of the present invention is to provide a signal emitter for emitting a warning or an emergency signal when required and having a testing device for testing the functions of the emitter.

In accordance with one aspect of the invention, there is provided an emitter comprising a housing, means for attaching the housing to a user, a control circuit received in the housing and including a first CPU, a memory coupled to the first CPU, a second CPU, a sensing circuit coupled to the second CPU for sensing a voltage supplied to the second CPU, an emitting circuit coupled to the first CPU for being actuated by the first CPU to emit a signal out. The housing includes a first switch and a second switch coupled to the first CPU for actuating the first CPU, and includes a third switch and a fourth switch coupled to the first CPU for information entering purposes. The emitting circuit sends out the signal when the first and the second switches are actuated, and the emitter may be tested with the first and the second switches.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
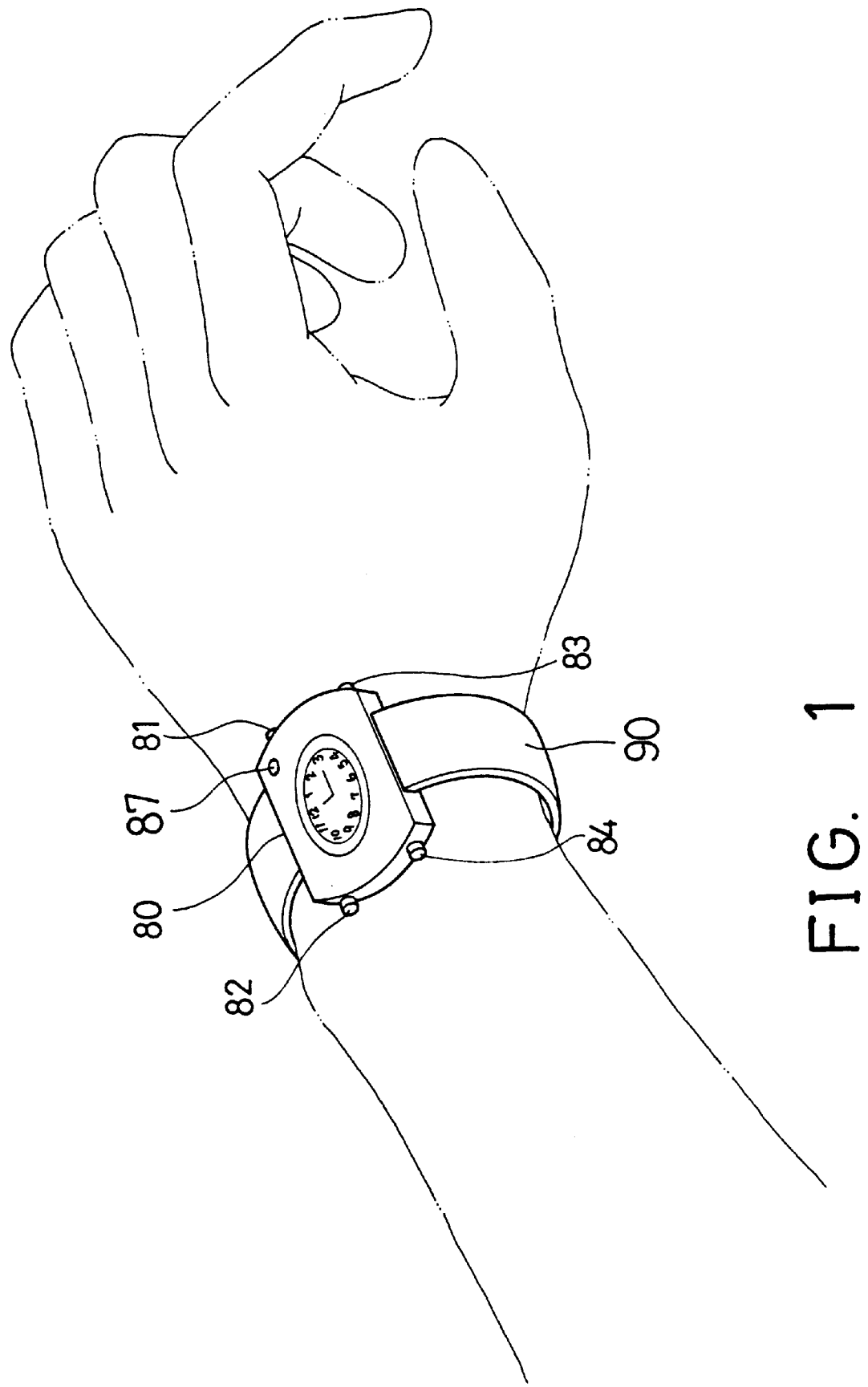
FIG. 1 is a perspective view showing a signal emitter in accordance with the present invention.

Referring to the drawings, and initially to FIG. 1, a signal emitter in accordance with the present invention comprises a watch type housing 80 having a fastening strap 90 or the like for securing or attaching the housing 80 onto the user, such as the hand of the user. The housing 80 includes two switches 81, 82 for testing purposes, and two further switches 83, 84 for input and output information from the signal emitter or for input information into the memory 40 via the CPU 20, and a light device, such as a light emitting diode (abbreviated as LED hereinafter) 87 for indicating the working or the operation of the signal emitter.

Figure 2:
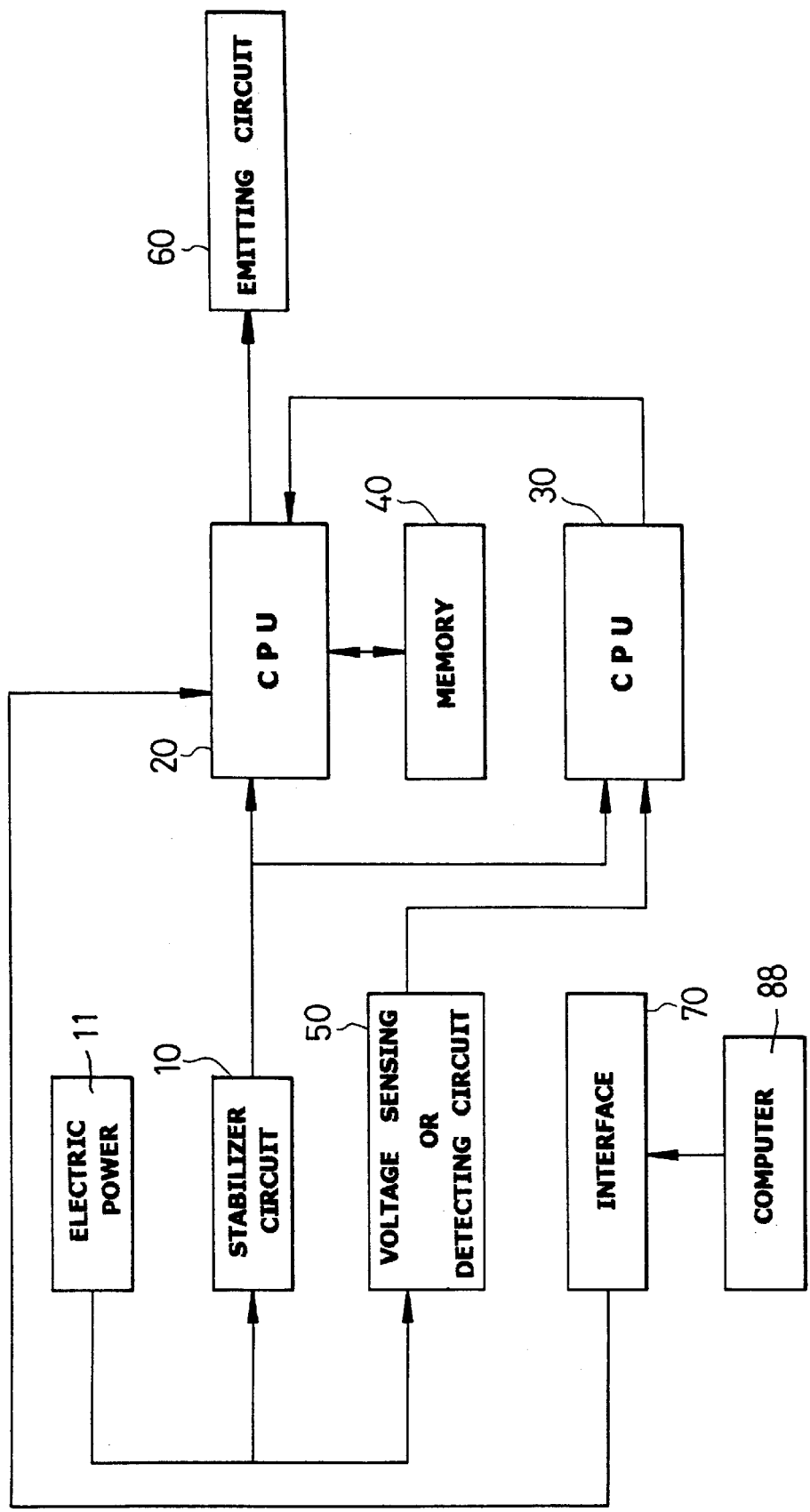
FIG. 2 is a block diagram showing the circuits and the devices of the signal emitter.
Figure 3:
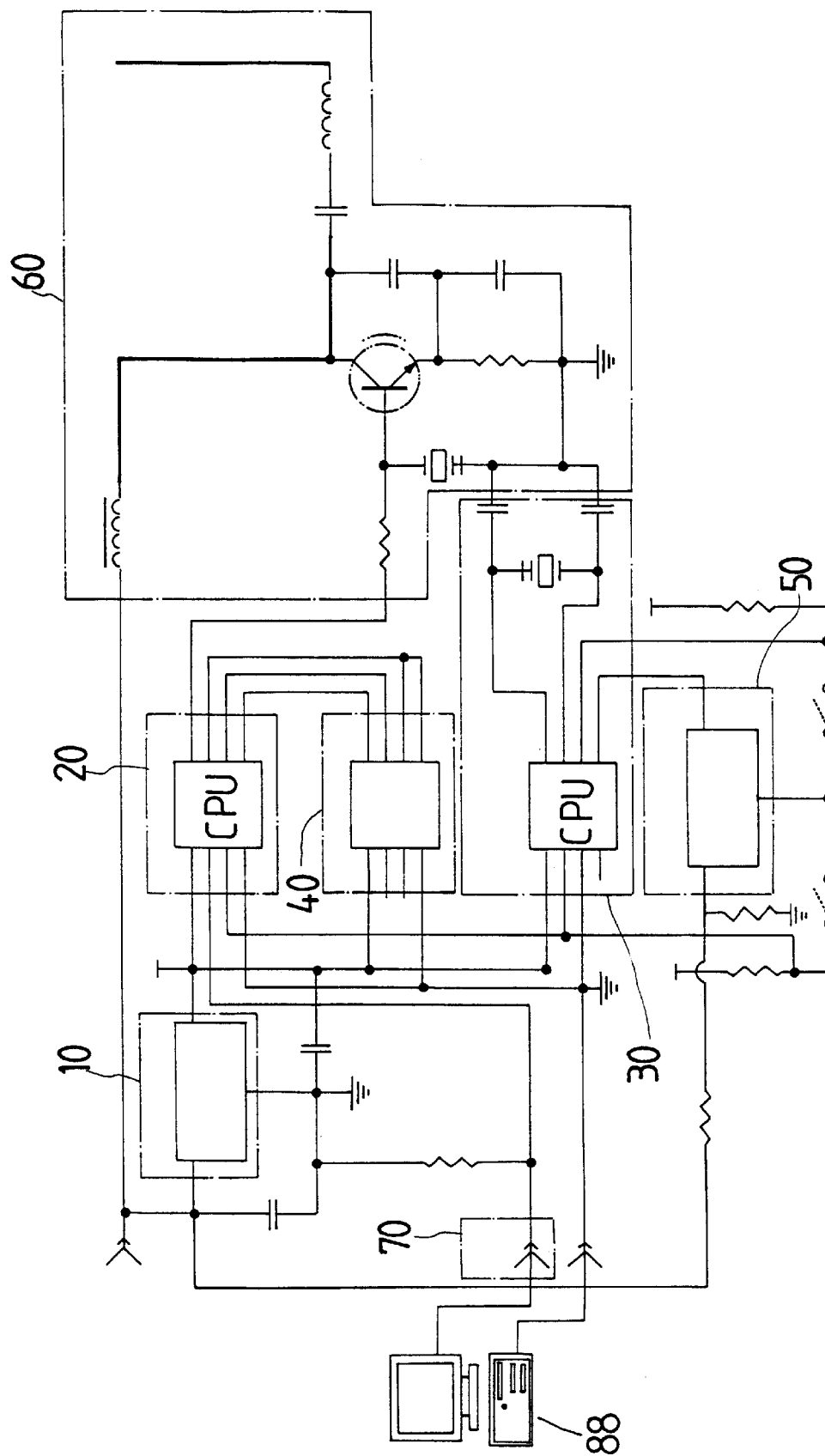
FIG. 3 is a circuit diagram showing the circuits of the signal emitter.

Referring next to FIGS. 2 and 3, the signal emitter comprises a microprocessor or a central processing unit (abbreviated as CPU hereinafter) 20, and a stabilizer circuit 10 coupled to the CPU 20 for supplying a stabilized electric power of the required voltage to the CPU 20. A memory 40 is coupled to the CPU 20 for storing words, codes or informations. Another CPU 30 is coupled to the CPU 20. A displayer and an input/output device (I/O) or a computer 88 is coupled to the CPU 20 via an interface 70 when required, for entering the information or the identification data of the user to the memory 40 via the CPU 20. A sensing circuit 50 couples the electric power 11 to the CPU 30 for sensing the voltage or the electric power supplied to the CPU 30. For example, when the voltage of the power supply is lower than the required value, such as 10V, the sensing circuit 50 may send a signal to the CPU 30 which will then send a signal to the CPU 20. The signal will then shown in the displayer for warning the user that the voltage of the power supply is short.

An emitting circuit 60, such as a high frequency emitting circuit, is coupled to the CPU 20 for receiving the signal from the CPU 20 or from the memory 40 and for transforming the signal to a radial frequency (RF) and for emitting the RF to a receiver. The receiver may be provided in a health care center or in a help center and may help the user when receiving the signal, such as the help or emergency signal, from the user, particularly the old people. The receiver is not related to the present invention and will not be described in further details. A vibration sensing device may be coupled to the CPU 30 for sensing the movement of the user and for sending the detected signal or the condition of the user to the CPU 30. The switches 81–84 may be coupled to the CPU 20 for controlling or for operating the CPU 20.

In operation, when the user has not been moved for a long time, such as 24 hours, for example, when the user or the old people may not move for a long time or when the old people is dead, the vibration sensing device may send out a signal to the CPU 30 which will then send out a signal to the CPU 20 in order to actuate the emitting circuit 60 to emit an emergency signal out to the receiver for asking help from the other people.

The switches 81–84 may be provided for controlling or for operating the CPU 20, such as for entering the instructions to the CPU 20. When the switches 81, 82 are depressed simultaneously by the user, for example, a signal for asking help from the others may be generated by the emitting circuit 60, and the LED 87 may generate an indicating light to indicate that the signal for asking help is being transmitted out. In addition, the switches 81, 82 may be used for detecting the functions or for setting the other functions of the signal emitter. For example:

(1) When the first switch 81 is depressed for more than 2 seconds, preferably about 3 seconds, after the LED 87 has flashed for one or more times, the second switch 82 is then depressed once, the LED 87 may flash once, the first switch 81 is then depressed once again, the LED 87 may also flash once, a timing function may then be set or switched on, for example, in order to emit a signal after a predetermined set or interval of time is reached.

(2) When the first switch 81 is depressed for more than 2 seconds (until or after LED flash), the second switch 82 is then depressed twice (LED flash each time the second switch 82 is depressed), the first switch 81 is then depressed once again, the LED 87 may flash twice, for example, then the timing function may then be released or switched off.

(3) When the first switch 81 is depressed for more than 2 seconds (until or after LED flash), the first switch 81 is then depressed once, when the LED flashes once, it represents that the timing function is switched on; and when the LED flashes twice, it represents that the timing function is switched off.

(4) When the first switch 81 is depressed for more than 2 seconds (until or after LED flash), the second switch 82 is then depressed three times (LED flash each time the second switch 82 is depressed), the first switch 81 is then depressed once again, the LED 87 will be energized to continuously generate a light, and the movement of the user may be detected to determine whether the user is moving or is alive or not. When the user does not move for a predetermined time of interval, such as ten minutes, a signal for asking help from the others may be generated by the emitting circuit 60.

(5) When the first switch 81 is depressed for more than 2 seconds (until or after LED flash), the second switch 82 is then depressed four times (LED flash each time the second switch 82 is depressed), the first switch 81 is then depressed once again, a low voltage signal may then be generated to test whether the low voltage signal may be emitted or not, the LED 87 may flash until the low voltage signal has been emitted and tested.

(6) When the first switch 81 is depressed for more than 2 seconds (until or after LED flash), the second switch 82 is then depressed five times (LED flash each time the second switch 82 is depressed), the first switch 81 is then depressed once again, a timing signal may then be generated to test whether the timing signal may be generated or emitted or not after a predetermined time of interval, the LED 87 may flash until the timing signal has been emitted and tested.

Accordingly, the emitter in accordance with the present invention may be used for emitting a warning or an emergency signal when required and having a testing device for testing the functions of the emitter.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. An emitter comprising:

a) a housing, b) means for attaching said housing to a user, c) a control circuit received in said housing and including a first CPU, a memory coupled to said first CPU, a second CPU, a sensing circuit coupled to said second CPU for sensing a voltage supplied to said second CPU, an emitting circuit coupled to said first CPU for being actuated by said first CPU to emit a signal out, d) said housing including a first switch and a second switch coupled to said first CPU for actuating said first CPU, and including a third switch and a fourth switch coupled to said first CPU for information entering purposes, said emitting circuit sending out the signal when said first and said second switches are actuated, and said emitter being tested with said first and said second switches.

* * * * *